(12) United States Patent
Gumaste et al.

(10) Patent No.: US 8,371,294 B2
(45) Date of Patent: Feb. 12, 2013

(54) METHOD AND APPARATUS FOR DRIVING A TRANSDUCER OF AN INHALATION DEVICE

(75) Inventors: Anand Gumaste, West Windsor, NJ (US); John Bowers, Clarksburg, NJ (US); Douglas Weitzel, Hamilton, NJ (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 1024 days.

(21) Appl. No.: 12/392,686

(22) Filed: Feb. 25, 2009

(65) Prior Publication Data

US 2009/0217925 A1 Sep. 3, 2009

Related U.S. Application Data

(60) Provisional application No. 61/032,883, filed on Feb. 29, 2008.

(51) Int. Cl.
*A61M 15/00* (2006.01)

(52) U.S. Cl. .......... 128/200.24; 128/200.14; 128/200.16

(58) Field of Classification Search ............. 128/200.16, 128/200.14, 203.12, 203.14, 203.15, 203.19, 128/200.24

See application file for complete search history.

(56) References Cited

U.S. PATENT DOCUMENTS

| | | | |
|---|---|---|---|
| 2,517,482 A | 8/1950 | Hall | |
| 3,507,277 A | 4/1970 | Altounyan et al. | |
| 3,518,992 A | 7/1970 | Altounyan et al. | |
| 3,635,219 A | 1/1972 | Altounyan et al. | 128/266 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,948,264 A | 4/1976 | Wilke et al. | 128/266 |
| 4,733,797 A | 3/1988 | Haber | 221/8 |
| 5,344,043 A | 9/1994 | Moulding et al. | 128/71 |
| 5,458,135 A | 10/1995 | Patton et al. | 128/200.14 |
| 5,487,378 A | 1/1996 | Robertson et al. | 128/200.16 |
| 5,884,624 A | 3/1999 | Barnett et al. | 128/206.24 |
| 5,906,202 A | 5/1999 | Schuster et al. | 128/203.23 |
| 6,367,470 B1 | 4/2002 | Denyer et al. | 128/200.14 |
| 6,629,646 B1 | 10/2003 | Ivri | 239/4 |
| 6,889,690 B2 | 5/2005 | Crowder et al. | 128/203.15 |
| 7,233,228 B2 | 6/2007 | Lintell | 340/309.7 |
| 7,318,434 B2 | 1/2008 | Gumaste et al. | 128/203.15 |
| 7,334,577 B2 | 2/2008 | Gumaste et al. | 128/203.15 |
| 7,538,473 B2 | 5/2009 | Blandino et al. | 310/317 |
| 7,607,435 B2 | 10/2009 | Lipp | 128/203.13 |
| 7,748,382 B2 | 7/2010 | Denyer et al. | 128/204.21 |
| 2002/0032409 A1 | 3/2002 | Ritsche | 604/154 |
| 2004/0055598 A1 * | 3/2004 | Crowder et al. | 128/203.15 |

(Continued)

FOREIGN PATENT DOCUMENTS

| | | |
|---|---|---|
| CN | 1668354 | 9/2005 |
| DE | 102005005540 | 8/2006 |

(Continued)

OTHER PUBLICATIONS

Search Report and Written Opinion dated Jul. 13, 2009.

(Continued)

*Primary Examiner* — Glenn Richman
(74) *Attorney, Agent, or Firm* — Hayes Soloway P.C.

(57) ABSTRACT

An inhaler is disclosed wherein medicament in a flat-bottomed container is aerosolized with a vibrator piezoelectric transducer. The transducer is driven by a signal that excites multiple harmonic frequencies to create a complex pattern of oscillations. A circuit for generating the drive signal to the transducer is also disclosed.

7 Claims, 3 Drawing Sheets

U.S. PATENT DOCUMENTS

Figure 1:
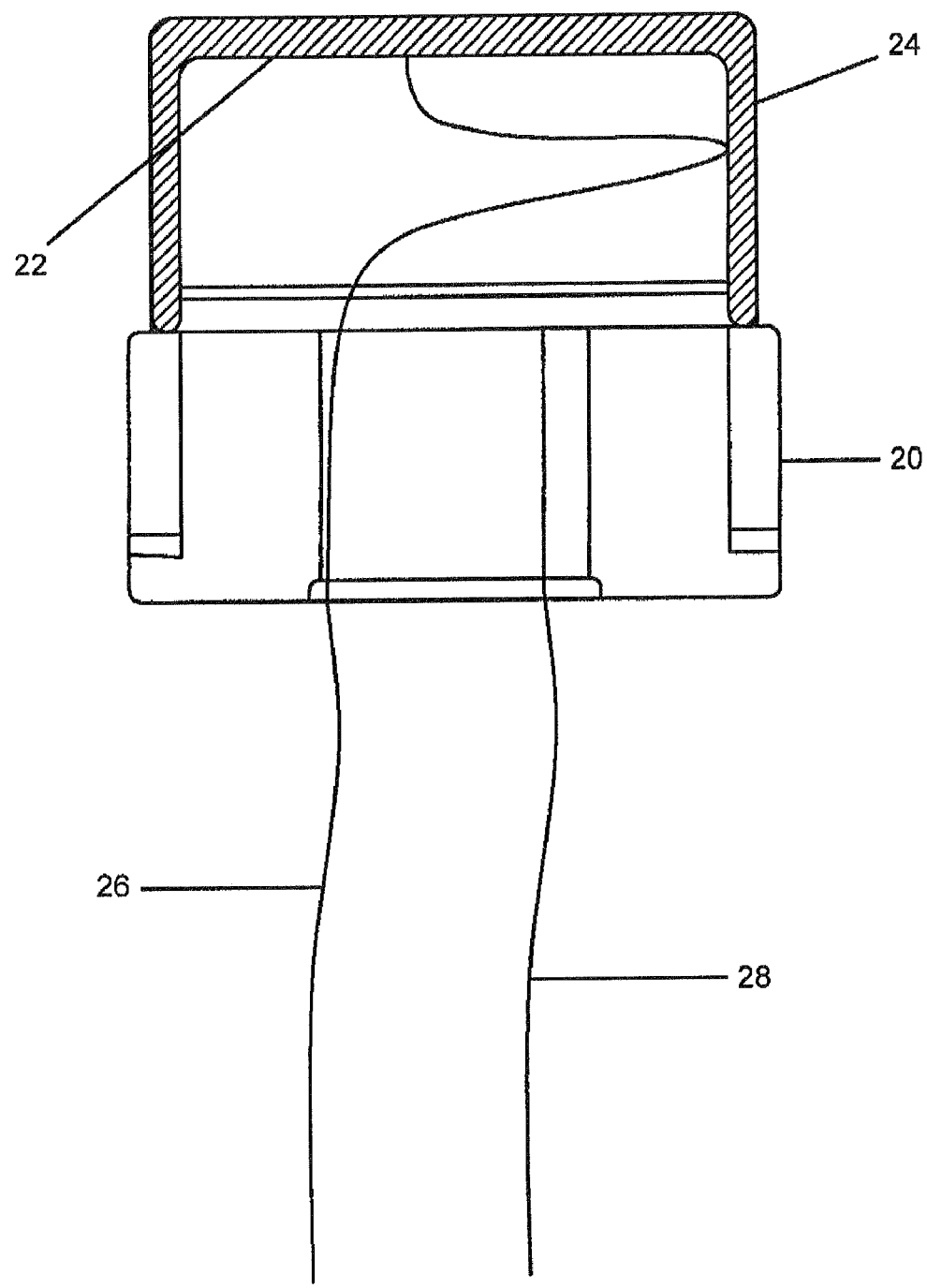

| | | |
|---|---|---|
| 2004/0250812 A1 | 12/2004 | Davies et al. ............ 128/200.14 |
| 2005/0121027 A1 | 6/2005 | Nilsson et al. ........... 128/200.23 |
| 2005/0155601 A1 | 7/2005 | Steiner et al. ............ 128/200.23 |
| 2005/0174216 A1 | 8/2005 | Lintell ..................... 340/309.16 |
| 2005/0267628 A1 | 12/2005 | Crowder et al. .............. 700/240 |
| 2006/0213503 A1 | 9/2006 | Borgschulte et al. .... 128/200.14 |
| 2006/0257327 A1 | 11/2006 | Zierenberg et al. ............. 424/46 |
| 2007/0059248 A1 | 3/2007 | Unger et al. ................. 424/9.52 |
| 2007/0137645 A1 | 6/2007 | Eason et al. ............ 128/203.15 |
| 2009/0020113 A1 | 1/2009 | Watanabe ................ 128/200.14 |
| 2009/0308390 A1 | 12/2009 | Smutney et al. ......... 128/203.15 |
| 2010/0139654 A1 | 6/2010 | Thoemmes et al. ..... 128/203.15 |
| 2010/0252032 A1 | 10/2010 | Thoemmes et al. ..... 128/200.23 |
| 2011/0041844 A1 | 2/2011 | Dunne ..................... 128/203.12 |

FOREIGN PATENT DOCUMENTS

| | | |
|---|---|---|
| DE | 102009005048 | 7/2010 |
| EP | 1 499 276 | 1/2005 |
| EP | 0 799 076 | 3/2005 |
| EP | 1 124 602 | 4/2005 |
| EP | 1 534 366 | 6/2005 |
| EP | 1 617 820 | 1/2006 |
| EP | 1 691 781 | 8/2006 |
| EP | 1 713 530 | 10/2006 |
| EP | 1 986 721 | 11/2008 |
| EP | 1 581 291 | 1/2009 |
| EP | 2 054 167 | 5/2009 |
| EP | 1 292 347 | 10/2009 |
| EP | 1 691 783 | 11/2009 |
| EP | 2 162 174 | 3/2010 |
| EP | 2 016 965 | 5/2010 |
| EP | 2 047 881 | 8/2010 |
| EP | 2 234 728 | 10/2010 |
| EP | 1 706 099 | 5/2011 |
| WO | WO 03/092576 | 11/2003 |
| WO | WO 03095010 | 11/2003 |
| WO | WO 2004/002394 | 1/2004 |
| WO | WO 2004/093848 | 11/2004 |
| WO | WO 2005/053646 | 6/2005 |
| WO | WO 2005/074455 | 8/2005 |
| WO | WO 2007/096111 | 8/2007 |
| WO | WO 2008/021281 | 2/2008 |
| WO | WO 2009/007068 | 1/2009 |
| WO | WO 2009/090084 | 7/2009 |
| WO | WO 2011/160932 | 12/2011 |
| WO | WO 2011/163272 | 12/2011 |

OTHER PUBLICATIONS

New Zealand Examination Report dated Sep. 14, 2011, issued in Patent Appln. No. 587432 (2 pgs).

Examination Report and translation issued in Microdose 07.06 Saudi Arabia, Appln. Serial No. 109300139 received Oct. 26, 2011 ( 6 pgs ).

Pakistan Examination Report English translation as reported by foreign agent (3 pages), issued in Pakistan Patent Application No. 171/2009.

Chilean Official Action + Translation dated Jan. 3, 2011 (7 pgs).

Official Action Microdose 07.06 Saudi Arabia, Appln. Serial No. 109300139 received Jun. 17, 2012 (5 pgs).

Chinese Office Action issued in related application No. 200980107038.6, dated Aug. 31, 2012 (8 pgs).

* cited by examiner

METHOD AND APPARATUS FOR DRIVING A TRANSDUCER OF AN INHALATION DEVICE

CROSS REFERENCE TO RELATED APPLICATIONS

This application claims priority from U.S. Provisional Application Ser. No. 61/032,883, filed Feb. 29, 2008.

FIELD OF THE INVENTION

The present invention relates generally to the field of inhalation devices, and more specifically, to inhalation devices that utilize vibration to facilitate suspension of particles of a medication into an inhaled gas stream (e.g., of inhaled air). The invention will be described in detail in connection with delivery of powdered medication to a patient, and will be described in connection with such utility, although other utilities, including specifically delivery of liquid droplets is contemplated.

BACKGROUND OF THE INVENTION

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles may develop an electrostatic charge on themselves during manufacturing and storage. This may cause the particles to agglomerate or aggregate, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10s of micrograms. For example, in the case of albuterol, a drug used in asthma, this is usually 25 to 50 micrograms. Current manufacturing equipment can effectively deliver aliquots of drugs in milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possess several disadvantages which are remedied by the inhalation devices of the present invention. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medicament. Also, such prior art devices result in uncontrolled amounts or clumps, of powdered material being inhaled into the user's mouth, rather than a constant inhalation of controlled amounts of finely dispersed powder.

The above discussion of the prior art is taken largely from U.S. Pat. No. 3,948,264 to Wilke et al, who discloses a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon rotation puts one or more holes in the capsule so that upon vibration of the capsule by an electromechanical vibrator, the powdered drug many be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule.

The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through an outlet channel and concurrent pressing of a switch to activate the electromechanical vibrating means, air is sucked through inlet channels and the air stream through a secondary inlet channel raises the capsule up against a vibrating plunger rod. The capsule is thus vibrated rapidly with powder being fluidized and dispensed from the pierced holes therein. (This technique is commonly used in manufacturing for dispensing powder through a hopper where the hopper is vibrated to fluidize the powder and move it through the hopper outlet. The pierced holes in the capsule represent the hopper outlet.) According to Wilke et al, the air stream through the inlet channels aids in withdrawal of powder from the capsule and carries this powder through the outlet channel to the mouth of the user. (Wilke et al, column 3, lines 45-55). Wilke et al further discloses that the electromechanical vibrator means may be placed at a right angle to the inlet chamber and that the amplitude and frequency of vibration may be altered to regulate dispensing characteristics of the inhaler.

Prior art devices such as above described have a number of disadvantages which makes them less than desirable for the delivery of dry powder to the lungs. Some of these disadvantages include:

The performance of the prior art inhalers depends on the flow rate generated by the user. Lower flow rate does not result in the powder being totally deaggregated and hence adversely affects the dose delivered to the patient.

Inconsistency in the bioavailability of the drugs from dose-to-dose because of lack of consistency in the deaggregation process.

Large energy requirements for driving the electromechanical based inhalers which increases the size of the devices making them unsuitable for portable use.

Loss of medication from opened or topped capsules.

Deterioration of medication in open or topped capsule due to exposure to oxygen or moisture.

In prior U.S. Pat. Nos. 7,318,434 and 7,334,577 incorporated herein by reference, and assigned to the common assignee MicroDose Technologies, Inc., there is provided an improvement over prior art inhalers that utilize vibration to facilitate suspension of power into an inhaled gas stream and which utilizes a synthetic jet to aerosolize drug powder from a blister pack or the like. As taught in the aforesaid U.S. Pat. Nos. 7,318,434 and 7,334,577 there is provided a dry powder inhaler having a first chamber such as a blister pack or other container, for holding a dry powder, and a second chamber connected to the first chamber via a passageway for receiving an aerosolized form of the dry powder from the first chamber and for delivering the aerosolized dry powder to a user. A vibrator is coupled to the dry powder in the first chamber. The vibrator is energized and coupled to the first chamber and drives the powder from the chamber by synthetic jetting.

The medicament for dry powder inhalers is commonly contained in a blister pack or other flat bottom container that is placed in contact with the face of a piezoelectric transducer or vibrator, whereupon the vibration energy of the transducer is transferred to the medicament particles. However, frictional losses between the engaging surface of the blister pack or other container and the face of the transducer may constrain movement of the transducer face and reduce the overall efficiency of the device.

SUMMARY OF THE INVENTION

The present invention provides an improvement over the prior art devices such as discussed above by providing an inhaler having a piezoelectric transducer for aerosolizing medicament contained in a blister pack or other flat bottom container, wherein the drive signal to the transducer has a waveform that excites both a primary and a secondary resonant frequency of the piezoelectric transducer. The preferred drive signal to the transducer should be one that comprises a waveform that has a fundamental frequency equal to the primary resonance frequency of the transducer and, in addition, significant energy at harmonics of the fundamental frequency.

Secondary resonant frequencies of the transducer are excited by the harmonics of the drive signal resulting in a more complex motion of the transducer face. The transducer face moves similar to the vibrating surface of a drum. This includes a considerable number of modes of vibration. The more complex movement of the transducer face causes the contact area between the engaging surface of the blister pack or other flat bottom container and the transducer face to be reduced, and in turn, the friction between the two surfaces also is reduced. This occurs primarily because of the tendency of the blister or container bottom to ride on the peaks of the deflection pattern of the transducer face and not to follow the complexity of its deformation due to the complex movement. A portion of the relative motion between the blister or container bottom and the transducer face is in the radial direction, necessitated by the changing radial dimension of the transducer face as it vibrates in a direction perpendicular to the plane of the face. This relative motion is necessary to avoid the significant energy loss that is associated with trying to periodically stretch the material that comprises the bottom surface of the container or blister pack such that it conforms to or remains firmly adhered to, i.e. in contact with the transducer face during vibration.

BRIEF DESCRIPTION OF THE DRAWINGS

Further features and advantages of the present invention will be seen from the following detailed description, taken in conjunction with the accompanying drawings, wherein:

FIG. 1 is a cross-sectional view of a piezoelectric actuator made in accordance with the present invention;

FIG. 2 is a graph showing the waveform of a drive signal for a piezoelectric transducer in accordance with the present invention;

FIG. 3 is a graph showing the harmonic energy of the piezoelectric transducer generated by the waveform shown in FIG. 2;

FIG. 4 is a graph showing the admittance of a piezoelectric transducer at various harmonic frequencies; and FIG. 5 is a schematic showing a drive circuit for a piezoelectric transducer in accordance with the present invention.

DETAILED DESCRIPTION OF PREFERRED EMBODIMENTS

In the following description, reference is made to the accompanying drawings, which form a part hereof, and in which is shown, by way of illustration, various embodiments of the present invention. It is understood that other embodiments may be utilized and changes may be made without departing from the scope of the present invention.

The present invention provides a method and device for delivering medicament to the lungs of a patient from an inhaler by using a piezoelectric transducer to deaggregate and aerosolize the medicament contained in a blister pack or the like. The piezoelectric transducer is activated by a drive signal which excites the transducer to vibrate at two or more different frequencies including its primary resonance frequency and at least one secondary frequency which is near a harmonic of the primary resonance frequency.

That is to say, the drive signal is chosen to excite secondary resonance frequencies of the piezoelectric transducer resulting in a complex pattern of deformation on the face of the transducer. Without being bound by theory, our observations suggest that the complex movement of the transducer face causes the surface area of the contact between the flat surface of the blister bottom in contact with the transducer face to be reduced, and by such a reduction, the friction between the two surfaces correspondingly reduced. This may occur because of the tendency of the blister bottom to ride on the peaks of the deflection pattern of the transducer face and not follow the complexity of its deformation due to the complex movement. This enables relative motion between the blister bottom and the transducer face in the radial direction, something that we have found necessary because of the changing radial dimension of the transducer face as it vibrates due to the elasticity of the material comprising the transducer face, such elasticity enabling the vibrating motion of the transducer. While not wishing to be bound by theory, our observations support the notion that such relative motion is necessary to avoid the significant energy loss that is associated with trying to periodically stretch the polymeric material that comprises the bottom of the blister bottom such that it conforms to or remains firmly adhered to, i.e. in contact with the transducer face during vibration.

Figure 2:
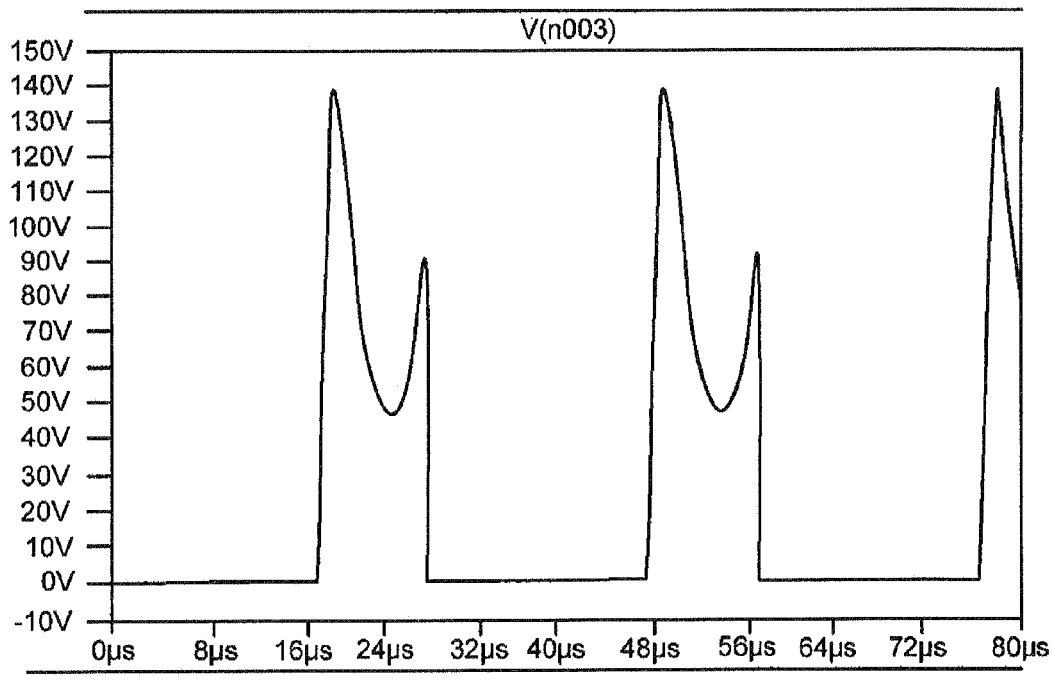

According to an exemplary embodiment of the present invention, the piezoelectric transducer is driven by a signal having a waveform as shown by in FIG. 2. This waveform is preferred for driving the motion described above in a piezoelectric transducer used in a dry powder inhaler by the assignee company. The piezo-electric transducer (FIG. 1) is a purpose designed transducer comprising an aluminum cylinder 20 that is 12.24 mm tall, and has an o.d. of 13.32 mm, that is closed at one end with a 0.25 mm thick piezoelectric disc 22 that in turn is attached to the flat surface of a cap 24 that is press-fitted into and that closes the cylinder 20. A positive lead wire 26 is soldered to the inside surface of the piezoelectric disc 22 and is adhered to the interior wall surface of the cap 24 using a silicone adhesive to provide strain relief. A negative lead wire 28 is attached to the aluminum cylinder 20.

Figure 3:
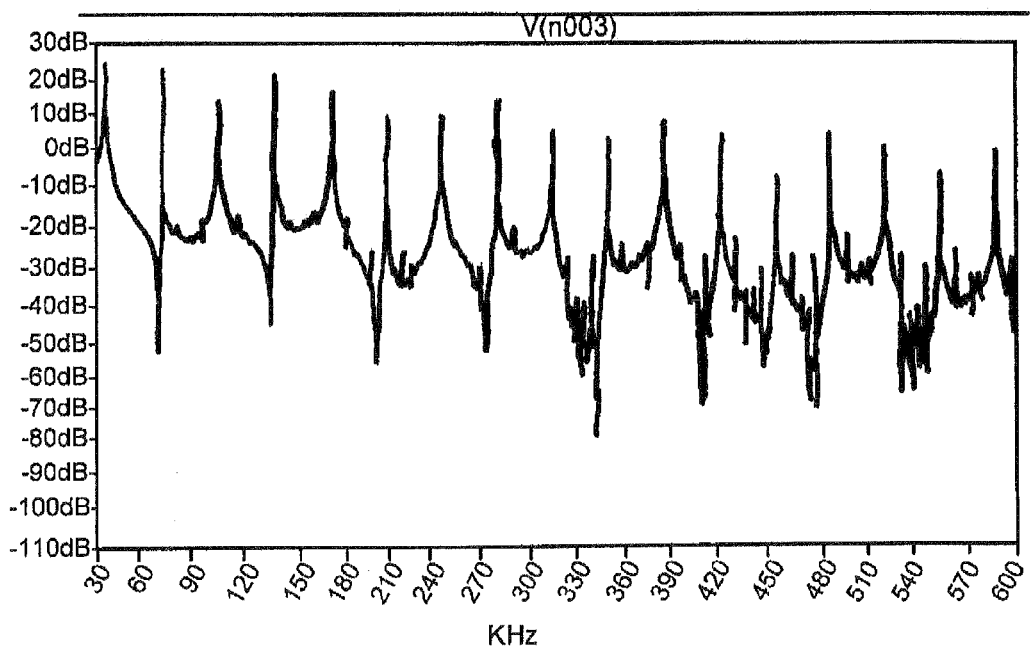

FIG. 3 is a plot of the harmonic energy of the waveform shown in FIG. 2. As can be seen, there is a considerable amount of harmonic energy generated by this waveform at each of the harmonics.

Figure 4:
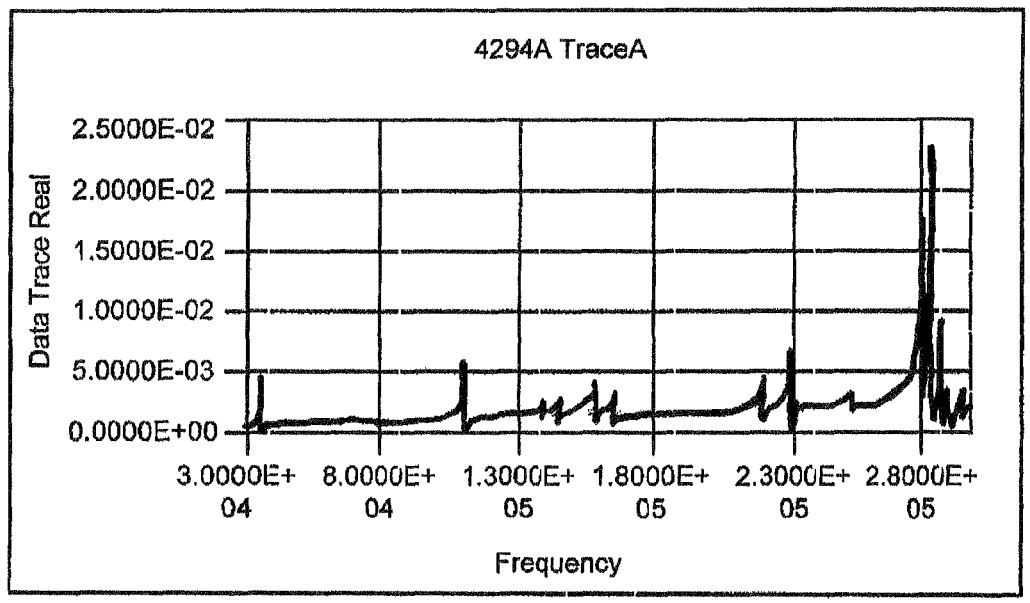

FIG. 4 shows the electrical admittance of the piezoelectric transducer used in the dry powder inhaler. The peaks in the admittance response indicate frequencies of mechanical resonance for the transducer. As can be seen, there are several points of significant mechanical resonance in addition to the primary resonance frequency of 35 kHz. Different piezoelectric transducers, however, may have different resonance frequencies. In our observations, we found that the aforesaid piezoelectric transducer was greatly excited at 285 kHz, which corresponds to the 8th harmonic of the drive waveform. Other transducers, however, may resonate strongly near other harmonics ($2^{nd}$, $4^{th}$, $6^{th}$, etc.) of the drive waveform, thereby performing in a manner similar to that found with the example transducer. Importantly, our experiments have consistently found that a drive signal with a high amount of harmonic energy is necessary to reliably create a strong synthetic jet for all combinations of transducer types and flat bottom blisters types that have been examined.

Figure 5:
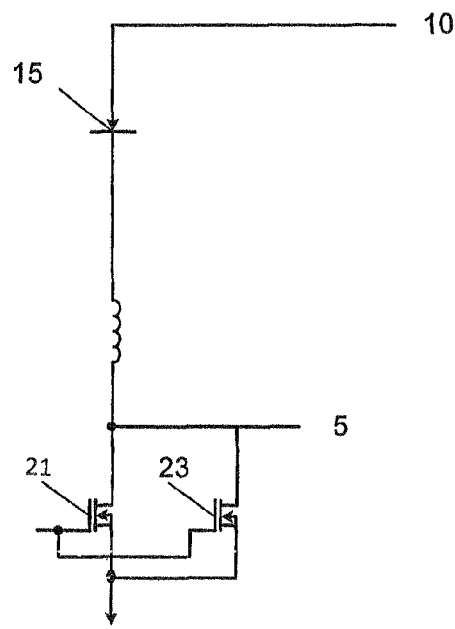

FIG. 5 is an example of a drive circuit that is capable of generating the preferred waveform of FIG. 2. The transducer 5 receives power from power supply 10. The field effect transistors 21, 23 comprise an electronic switch that is opened and closed at the primary resonance frequency of the transducer. Alternatively, the drive circuit may be constructed with a single transistor. Inductor 12 stores energy when the electronic switch is closed. When the electronic switch is open, all of the energy in the inductor 12 is transferred to the piezoelectric transducer 5. The diode 15 effectively disconnects the inductor from the transducer after the energy of the inductor has been transferred to the transducer, thereby insuring the maximum energy transfer during a cycle.

Other waveforms may also be used. The primary requirement is that the drive waveform produce sufficient harmonic energy such that a secondary resonant frequency of the piezoelectric transducer is excited whereby a mechanical oscillation at the secondary resonance occur. It also is possible to generate a waveform comprising two sinusoidal signals at two different frequencies corresponding to the primary and a secondary resonance frequency of the transducer. Any signal that has sufficient energy at both the primary and a secondary resonance frequency such that significant mechanical motion of the transducer face is created at both frequencies creates the motion of the piezoelectric transducer face that has the desired effect of minimizing the friction between the transducer face and the blister bottom.

It should be emphasized that the above-described embodiments of the present device and process, particularly, and "preferred" embodiments, are merely possible examples of implementations and merely set forth for a clear understanding of the principles of the invention. Many different embodiments of the invention described herein may be designed and/or fabricated without departing from the spirit and scope of the invention. All these and other such modifications and variations are intended to be included herein within the scope of this disclosure and protected by the following claims. Therefore the scope of the invention is not intended to be limited except as indicated in the appended claims.

The invention claimed is:

1. A method of driving a transducer in an inhaler, having a piezoelectric transducer as a vibrator, which comprises providing a signal comprising a waveform that has a fundamental frequency equal to a primary frequency of the transducer to produce oscillations, the signal exciting the primary resonant frequency of the transducer and, in addition, at least one secondary resonant frequency of the transducer.

2. The method of claim 1, wherein the signal is a waveform comprising two sinusoidal signals at two frequencies corresponding to the primary resonant frequency and the secondary resonant frequency.

3. The method of claim 1, wherein the transducer is used to aerosolize medicament contained in a blister pack.

4. The method of claim 3, wherein friction between the blister pack and the transducer due to the oscillations is minimized.

5. The method of claim 3, wherein the medicament is a dry powder.

6. The method of claim 3, wherein the medicament is a liquid.

7. The method of claim 1, wherein the transducer resonates at an nth harmonic of its primary resonance frequencies, wherein n is a whole number selected from the group consisting of 2, 4, 6 and 8.

* * * * *